United States Patent
Chapples et al.

(10) Patent No.: US 8,252,158 B2
(45) Date of Patent: Aug. 28, 2012

(54) OXYGEN SENSORS

(75) Inventors: John Chapples, Drayton (GB); John Anthony Tillotson, Parkstone (GB); Ian McLeod, Boyatt Wood (GB); Martin Williamson, Oakdale (GB)

(73) Assignee: Honeywell International Inc., Morristown, NJ (US)

( * ) Notice: Subject to any disclaimer, the term of this patent is extended or adjusted under 35 U.S.C. 154(b) by 660 days.

(21) Appl. No.: 11/877,331

(22) Filed: Oct. 23, 2007

(65) Prior Publication Data
US 2008/0202929 A1 Aug. 28, 2008

Related U.S. Application Data

(60) Provisional application No. 60/863,859, filed on Nov. 1, 2006.

(51) Int. Cl.
*G01N 27/413* (2006.01)
(52) U.S. Cl. ........ 204/408; 204/409; 204/415; 204/432; 205/783
(58) Field of Classification Search .............. 204/400, 204/415, 408–409, 418–419, 424, 432; 205/775, 205/782.5, 783, 784–785.5
See application file for complete search history.

(56) References Cited

U.S. PATENT DOCUMENTS

| | | |
|---|---|---|
| 4,159,234 A | 6/1979 | Eifler et al. |
| 4,277,323 A | 7/1981 | Muller et al. |
| 4,334,974 A | 6/1982 | Muller et al. |
| 4,368,696 A * | 1/1983 | Reinhardt ..................... 123/3 |
| 4,386,858 A | 6/1983 | Kude et al. |
| 4,444,337 A | 4/1984 | Kude et al. |
| 4,502,939 A | 3/1985 | Holfelder et al. |
| 4,695,361 A * | 9/1987 | Grady ........................ 204/415 |
| 4,824,550 A | 4/1989 | Ker et al. |
| 4,900,412 A | 2/1990 | Ker et al. |
| 5,098,548 A | 3/1992 | Duce |
| 5,387,329 A | 2/1995 | Foos et al. |
| 5,401,376 A | 3/1995 | Foos et al. |
| 5,425,268 A | 6/1995 | Li et al. |
| 5,503,719 A | 4/1996 | Foos et al. |
| 5,518,601 A | 5/1996 | Foos et al. |
| 5,595,646 A | 1/1997 | Foos et al. |
| 5,623,105 A | 4/1997 | Liston et al. |
| 5,668,302 A | 9/1997 | Finbow et al. |
| 5,746,899 A | 5/1998 | Finbow et al. |
| 5,746,900 A * | 5/1998 | Venkatasetty ............... 204/415 |
| 5,761,952 A | 6/1998 | Gilby et al. |
| 5,795,454 A | 8/1998 | Friese et al. |
| 5,801,317 A | 9/1998 | Liston et al. |
| 5,827,415 A | 10/1998 | Gur et al. |
| 5,830,337 A * | 11/1998 | Xu ............................ 204/400 |

(Continued)

OTHER PUBLICATIONS

International Search Report for PCT/US07/82483, dated May 16, 2008 (2 pages).

*Primary Examiner* — Kaj K Olsen
*Assistant Examiner* — Susan D Leong
(74) *Attorney, Agent, or Firm* — Husch Blackwell LLP

(57) ABSTRACT

An electrochemical oxygen sensor includes a micro-porous plastic membrane supported on a sealing disk and located between a gas inflow port and the sensor's electrolyte. The membrane and disk minimize thermal shock effects due to using the sensor at a first location, at a first temperature, and then moving it to a second location at a different temperature.

17 Claims, 2 Drawing Sheets

U.S. PATENT DOCUMENTS

| | | | |
|---|---|---|---|
| 5,846,391 A | 12/1998 | Friese et al. | |
| 5,942,092 A | 8/1999 | Weyl et al. | |
| 5,949,023 A | 9/1999 | Weyl | |
| 6,015,540 A | 1/2000 | McAdams et al. | |
| 6,024,853 A | 2/2000 | Kiesele et al. | |
| 6,068,748 A | 5/2000 | Berger et al. | |
| 6,081,736 A | 6/2000 | Colvin et al. | |
| 6,092,430 A | 7/2000 | List | |
| 6,179,986 B1 | 1/2001 | Swette et al. | |
| 6,206,377 B1 | 3/2001 | Weyl | |
| 6,273,432 B1 | 8/2001 | Weyl et al. | |
| 6,474,655 B1 | 11/2002 | Weyl et al. | |
| 6,512,939 B1 | 1/2003 | Colvin et al. | |
| 6,993,955 B1 | 2/2006 | King et al. | |
| 7,010,957 B2 | 3/2006 | Williams et al. | |
| 7,122,101 B2 | 10/2006 | Gonsior | |
| 7,138,270 B2 | 11/2006 | Papkovsky et al. | |
| 2002/0176617 A1* | 11/2002 | Simonetti | 382/141 |
| 2003/0221494 A1 | 12/2003 | Gonsior | |
| 2004/0096723 A1* | 5/2004 | Debe et al. | 429/35 |
| 2004/0241783 A1 | 12/2004 | Papkovsky et al. | |
| 2006/0213771 A1 | 9/2006 | Routbort et al. | |

\* cited by examiner

OXYGEN SENSORS

CROSS-REFERENCE TO RELATED APPLICATION

This application claims the benefit of the filing date of U.S. Provisional Application Ser. No. 60/863,859 filed Nov. 1, 2006 and entitled "Oxygen Sensors".

FIELD

The invention pertains to electrochemical gas sensors. More particularly, the invention pertains to electrochemical oxygen sensors which are resistant to thermal shock.

BACKGROUND

Electrochemical sensors are known and can be used to detect various types of gases including oxygen as well as other types of gases.

Representative sensors have been disclosed in U.S. Pat. No. 5,668,302 to Finbow et al. entitled Electrochemical Gas Sensor Assembly, issued Sep. 16, 1997, and U.S. Pat. No. 5,746,899 to Finbow et al. entitled Electrochemical Gas Sensor, issued May 5, 1998. The '302 and '899 patents have been assigned to the assignee hereof and are incorporated by reference. Useful as they have become, such sensors are not without some limitations.

A fairly common problem experienced by users of portable oxygen gas detection equipment is that the instrument can be susceptible to thermal shock and generate false alarms when the user moves between locations at different temperature. Typical conditions that might generate the false alarm condition would be when the user exits a heated office or calibration station into a cold working environment.

This situation is most noticeable in winter when the temperature difference often exceeds 30° C. Whilst the effect is often associated with a negative temperature change i.e. movement from a warm to cooler environment, the same effect can also manifest itself in the opposite sense when there is a positive temperature change.

Thermal shock in an oxygen sensor or cell is usually characterized by a rapid change in output response other than that caused by normal diffusion, when a change in temperature is experienced by the cell. Thermal shock does not always happen immediately and thermal shocks have been noticed after time periods of over one hour after the initial temperature change occurred. This has implications in a finished product of false alarms where a false oxygen level is registered by the cell.

The cause of the problem is related to the design and construction of the oxygen sensor which relies on controlled diffusion of oxygen into the sensor from the external environment via a capillary hole. Once oxygen has entered the cell it reacts and generates a current that is proportional to the oxygen concentration in the external environment.

Large temperature excursions can cause an additional contribution to the signal when the internal cell pressure (caused by the temperature change) equilibrates with the environment. The causes of these pressure differences include air, or, gas pockets within the body of the cell which expand or contract with temperature.

For the typical condition described above, the gas inside the cell contracts when the instrument is transferred to the cold environment. The pressure difference caused through contraction draws air into the cell through the capillary leading to an enhanced cell output and false alarm.

Thus, there continues to be a need for improved oxygen sensors which minimize false alarms. Preferably such improved functionality could be achieved without substantially increasing the manufacturing complexity and cost of such units.

Also, it would be preferable if such improved detectors could be implemented as portable or human wearable to facilitate use.

DETAILED DESCRIPTION

Figure 1:
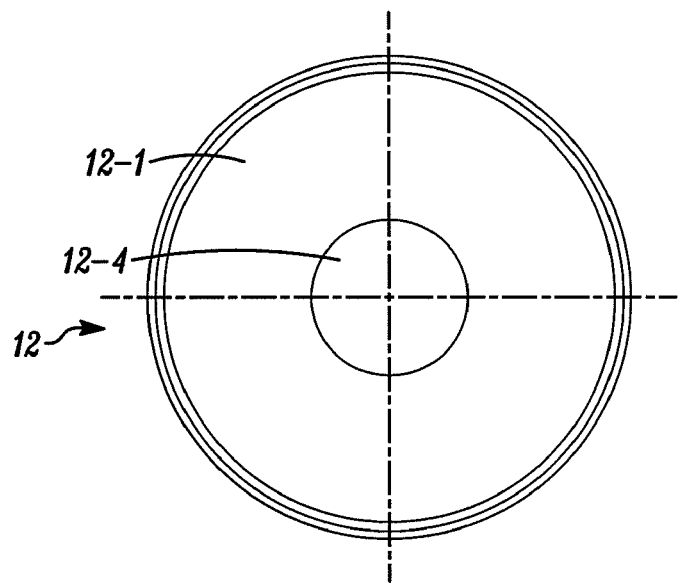
FIG. 1 is a plan view of a sealing disk according to one embodiment of the present invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the invention solve the thermal shock problem by creating a partition in the cell that prevents bulk flow or exchange of air between the cell and the environment. In a preferred embodiment of the invention, the partition comprises a micro-porous plastic membrane supported on a compressible foam adhesive gasket which is itself supported on a rigid plastic perforated disk.

The disk serves a number of functions. The primary role is to support the foam gasket and membrane. Additionally, an air tight seal can be formed between the plastic disk and the cell body or housing. This is achieved, in a disclosed embodiment, by ultrasonically welding the plastic disk to the main outer plastic body of the cell. The weld also serves to form an air tight seal around the metallic current collector strip that passes between both compartments within the cell.

It is preferable that the membrane be adequately supported and not be able to deform or flex under pressure, since this behavior can also generate pressure transient effects of sufficient magnitude to cause false alarms. The disk can be annular with a hole in the middle to allow electrolyte ions to pass through the partition between the upper and lower compartments of the cell thereby facilitating normal operation of the cell. Alternatively the single central hole in the disk could be replaced with a plurality of smaller holes, each also capable of allowing electrolyte transport across the disk to the electrode from the main body of the cell.

The function of the micro-porous membrane is to prevent the bulk transport of gas (usually in the form of bubbles) through the cell. It relies on the fact that liquid is held in the pores of the membrane by surface tension and capillary action, and that pressure must be applied to overcome these forces before bubbles/air are able to cross the membrane. The minimum pressure (bubble point pressure) required to force the liquid out of the membrane pores is related to the membrane capillary geometry according to the following equation; $P=(4k\cos\theta\sigma)/d$ where P is the bubble point pressure, d is the pore diameter, k is a geometry correction factor, θ is the liquid solid contact angle and σ is the surface tension. Therefore if a membrane material is chosen with pores of sufficiently small diameter, the pressure required for gas to cross the membrane will exceed that created by environmental temperature changes, thereby eliminating the temperature transient effect.

An estimate of the pressure difference that the membrane needs to withstand to eliminate the problem can be calculated from the gas law (PV=nRT). Where P, V, T, and n are pressure, volume, temperature, and amount of gas with R as the gas constant. For a 40° C. temperature reduction the internal cell pressure decreases by 13.3% which is equivalent to 0.133 bar. Therefore a suitable membrane material can be expected to have a minimum bubble point pressure of at least 0.13 bar. In practice materials are chosen with values that exceed this.

The compressible foam gasket serves two purposes. The adhesive surfaces ensure an air tight seal between the supporting shelf and the membrane material; in addition the compressible nature of the material ensures that any "dead volume" in the upper partition is minimized. The amount of free "dead volume" in the upper partition is associated with the size of the initial thermal transient that all lead based oxygen sensors show on rapid changes of temperature.

Embodiments of the invention include a micro-porous plastic membrane material. The membrane material is not swelled or deformed by electrolyte, nor chemically degraded by electrolyte, or reaction products of oxygen reduction.

The Micro-pores in the membrane also allow transport of ions through the film unlike some solid membranes which only allow water migration. Therefore the membrane material does not promote osmosis which may under certain circumstances prove to be an issue.

Use of a plastic support disk, or plate, as in FIG. 1, which can be ultrasonically welded to a cell body to provide air tight seal with the body and current collector, improves cell reliability and life-time. The disk also stops the membrane from flexing under pressure. Use of a compressible gasket minimizes "dead volume" in a cap or cover for the cell thereby reducing initial thermal transient effects.

Figure 2:
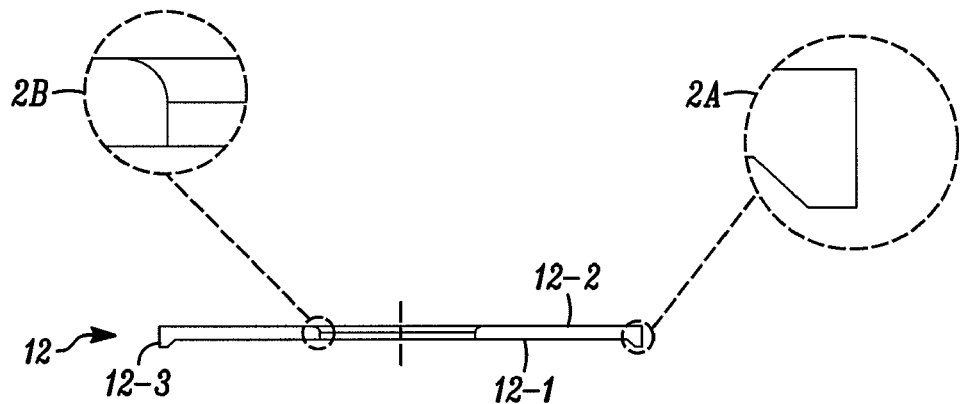
FIG. 2 illustrates a side elevational view of a sealing disk as in FIG. 1.
Figure 2A:
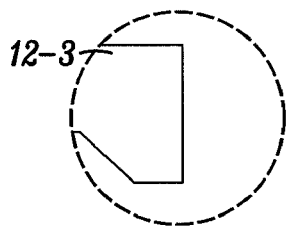
FIG. 2A is an enlarged partial view of an edge of the disk of FIG. 2.
Figure 2B:
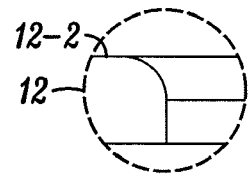
FIG. 2B is an enlarged partial view of a central region of the disk of FIG. 2.

FIGS. 1, 2-2B illustrate various aspects of a disk or partition 12 in accordance with the invention. As illustrated therein, disk 12 is a rigid, generally annular shaped member with first and second spaced apart planar surfaces 12-1, 12-2 bounded by a peripheral support 12-3. The disk 12 has a central opening 12-4. The disk 12 carries a compressible foam adhesive gasket 14. The gasket in turn carries a selected micro-porous plastic membrane 16.

As noted above, the disk 12 can be ultrasonically welded to an external housing of a respective oxygen sensor. The sensor may include a hollow housing which carries at least one electrode. The housing defines a gas inflow port and a micro-porous planar membrane closing the housing between the gas inflow port and a counter electrode to regulate an inflow of ambient gas. As will be understood by those of skill in the art, disk 12 could alternately be perforated by one or more openings therethrough. The openings need not be centrally located, but could be distributed across the disk. Alternately, disk 12 could be formed of a material permeable to a selected electrolyte.

Figure 3:
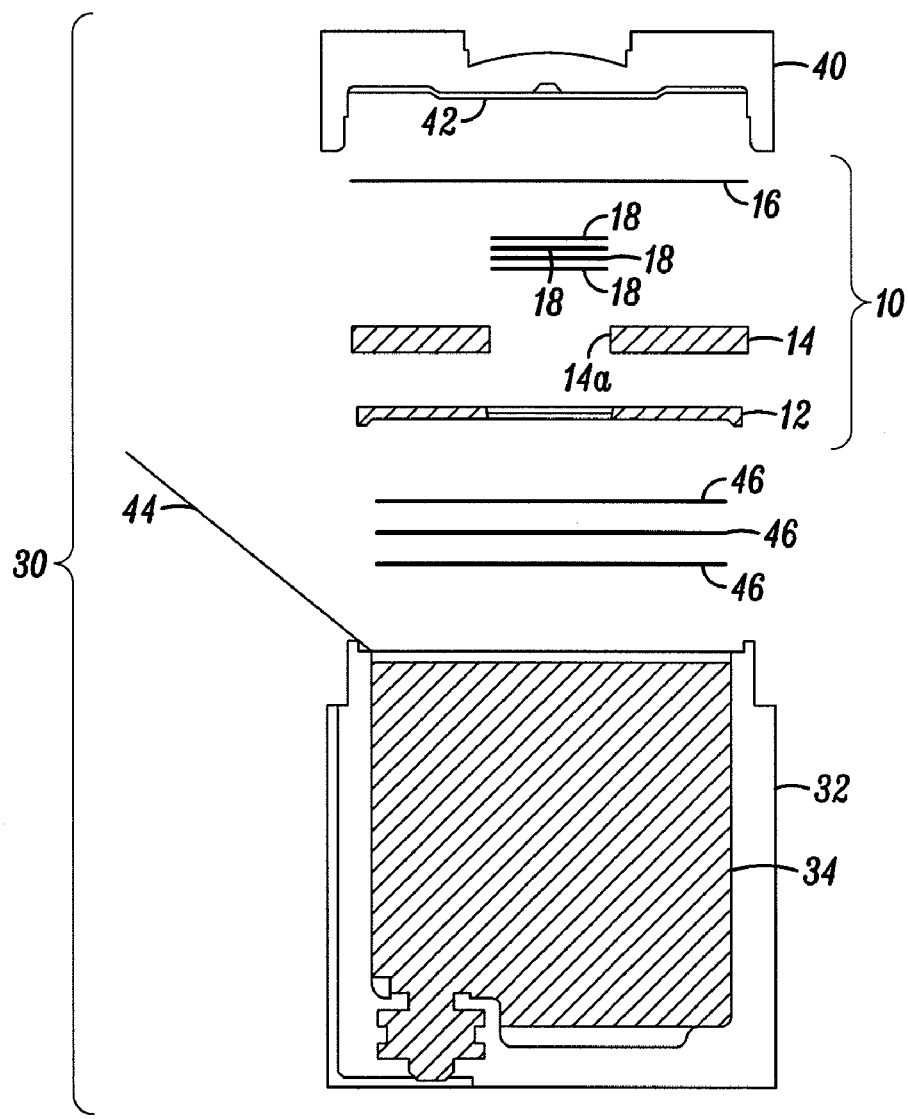
FIG. 3 is an exploded view that illustrates the components of an oxygen cell according to one embodiment of the present invention.

FIG. 3 is an exploded view of a representative oxygen sensor 30 which embodies the present invention. The sensor may include sensing and counter electrodes. The cell 30 includes a hollow, cylindrical body 32 which defines an interior region 34 for an electrolyte for the cell. The body of electrolyte may be in contact with one of the electrodes.

A top end 36 of the body 32 defines an annular region indicated generally at 38 which can receive and support a multiple element separator filter 42. The cell body or housing is closed with a cover with a gas inflow port.

The sealing disk 12 as previously discussed, is supported by the annular surface 38 and can be ultrasonically welded to the body 32. The compressible foam adhesive gasket 14, also annular in shape, having a central opening 14a, overlays and is supported by the disk 12. Filter 18 fills the opening 14a of the gasket 14.

Membrane 16 overlays the gasket 14. The cell 30 is closed with a cap 40 which could be affixed to the body 32 by welding or adhesive. The cap 40 can carry a working electrode 42 including at least one of a sensing and counter electrode. The body 32 can carry an internal current collector element 44.

In assembling one embodiment of the present invention, as in FIG. 3, the plurality of separator filters 42 is located centrally on the top of the cell body molding 32. The plastic sealing disk, 12, as in FIG. 1 for example, is then placed centrally within the recess 38 of the body molding 32 on top of the separator filters 42 ensuring that the internal current collector 44 is located between the plastic sealing disc 12 and body molding 32. The sealing disc 12 is then ultrasonically welded to the body molding 32.

An adhesive foam annulus 14, such as a closed cell EPDM, is located centrally on the plastic sealing disk 12. A plurality of small separator filters 18 is then located in the opening 14a formed by the annular foam gasket 14 and plastic sealing disc 12. The micro-porous membrane 16 is located centrally on top of the adhesive foam disc or gasket 14.

The internal current collector 44 is then folded over the nylon ionic membrane 16. The pre-assembled cap molding 40 and working electrode 42 is then placed on to the cell body assembly 32 and ultrasonically welded into place to complete cell 30.

Embodiments of the invention remove thermal shock within an oxygen cell by sealing the lead chamber of the cell from the working electrode preventing gas transfer between the two. Thermal transients (The initial peak in cell output when exposed to a sudden reduction in temperature) can be reduced by removing free volume and therefore trapped gas in the top half of the cell within the area between ionic membrane and working electrode.

By using a plastic disc such as disk 12 as a support for a nylon membrane, such as membrane 16 and welding the disc to the body 32 of the oxygen cell such as cell 30 it is possible to create a gas tight seal between upper and lower parts of the cell and remove thermal shock effects that are caused by transfer of gas between the two parts. Further, by using an EPDM Closed foam gasket, such as gasket 14, between the plastic disc 12 and membrane 16 it is possible to lower the amount of free volume in the top part of the cell 30 and therefore lower the initial thermal transient.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. An electrochemical gas sensor comprising:
   a body having first and second chambers located inside the body separated by an opening that is also located inside the body;

a working electrode disposed within one of the chambers; and a sealing member disposed over the opening between the first and second chambers, the sealing member, in turn, having at least one opening therethrough and an overlying micro-porous membrane carried therein to minimize temperature based shocks, said micro-porous membrane allowing electrolyte ions to pass through the micro-porous membrane and preventing the bulk transport of gas and exchange of air between the first and second chambers, said micro-porous membrane holding liquid in the pores of the micro-porous membrane by surface tension and capillary action and wherein pressure must be applied across the micro-porous membrane between the first and second chambers to overcome the surface tension and the capillary action before gas is able to cross the sealing member between the first and second chambers, the micro-porous membrane having a bubble point pressure of at least 0.13 bar.

2. An electrochemical gas sensor as in claim 1 wherein the working electrode further comprises at least one of a sensing electrode and a counter electrode.

3. An electrochemical gas sensor as in claim 1 where the micro-porous membrane is positioned in the sensor between a counter electrode and a gas inflow port.

4. An electrochemical gas sensor as in claim 3 which includes a compressible gasket which carries the micro-porous membrane.

5. An electrochemical gas sensor as in claim 1 which includes a compressible foam adhesive gasket which carries the membrane.

6. An electrochemical gas sensor comprising a hollow housing having first and second chambers, at least one of which carries at least one electrode and which includes an inwardly extending, annular support surface located inside the hollow housing between the first and second chambers for a sealing member, a gasket and a micro-porous membrane, the micro-porous membrane allowing electrolyte ions to pass through the micro-porous membrane between the first and second chambers and preventing the bulk transport of gas and exchange of air between the first and second chambers, said micro-porous membrane holding liquid in the pores of the micro-porous membrane by surface tension and capillary action and wherein pressure must be applied across the micro-porous membrane to overcome the surface tension and the capillary action before gas is able to cross the micro-porous membrane, the micro-porous membrane having a bubble point pressure of at least 0.13 bar.

7. An electrochemical gas sensor as in claim 6 where the gasket carries the micro-porous membrane.

8. An electrochemical sensor as in claim 7 with the sealing member comprising a generally planar structure fixedly attached to the hollow housing.

9. An electrochemical gas sensor as in claim 6 where the housing carries the sealing member, the gasket and the membrane in a multi-layer, stacked configuration.

10. An electrochemical gas sensor as in claim 9 where the housing is closed with a cover with a gas inflow port, the cover being adjacent to the micro-porous membrane, the sealing member being adjacent to an internal region in the housing and to an electrode.

11. A portable oxygen sensor which comprises a hollow housing having first and second chambers; the housing carrying at least sensing and counter electrodes; a body of electrolyte in contact with one of the electrodes; the housing defining a gas inflow port; and a micro-porous planar membrane located within an interior of the hollow housing closing the interior of the housing between the first and second chambers and between the inflow port and a counter electrode to regulate an inflow of ambient gas, said micro-porous membrane allowing electrolyte ions to pass through the micro-porous membrane and preventing the exchange of air between the first and second chambers, the micro-porous membrane holding liquid in the pores of the micro-porous membrane by surface tension and capillary action and wherein pressure must be applied across the micro-porous membrane to overcome the surface tension and the capillary action before gas is able to cross the micro-porous membrane, the micro-porous membrane has a bubble point pressure of at least 0.13 bar.

12. An oxygen sensor as in claim 11 which includes a compressible gasket which carries the micro-porous membrane.

13. An oxygen sensor as in claim 12 wherein the housing carries an internal support member for the gasket, the support member contributing to a gas tight seal between the inflow port and an internal region of the housing.

14. An oxygen sensor as in claim 13 where the electrolyte is adjacent to the support member and in the internal region of the housing.

15. An oxygen sensor as in claim 14 where the support member includes an annular plastic element to which the gasket can be attached where the annular element can be sealed to a portion of the housing adjacent to the internal region.

16. An oxygen sensor as in claim 13 where the support member is one of perforated, or, permeable to a selected electrolyte carried in the housing.

17. An oxygen sensor as in claim 16 where the support member comprises one of an annular disk, or a disk exhibiting a plurality of spaced apart openings therethrough.

* * * * *